US009636259B2

(12) United States Patent
Henry et al.

(10) Patent No.: US 9,636,259 B2
(45) Date of Patent: May 2, 2017

(54) WATER RESISTANT ACOUSTIC PORT IN EAR-MOUTHED HEARING DEVICE

(71) Applicant: 3M INNOVATIVE PROPERTIES COMPANY, St. Paul, MN (US)

(72) Inventors: Paul D. Henry, Carmel, IN (US); David M. Lutgring, Indianapolis, IN (US); David A. Hotvet, Savage, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 14/798,516

(22) Filed: Jul. 14, 2015

(65) Prior Publication Data
US 2016/0030246 A1 Feb. 4, 2016

Related U.S. Application Data

(60) Provisional application No. 62/031,449, filed on Jul. 31, 2014.

(51) Int. Cl.
*A61F 11/06* (2006.01)
*A61F 11/08* (2006.01)
*H04R 1/10* (2006.01)
*H04R 25/00* (2006.01)

(52) U.S. Cl.
CPC ............ *A61F 11/08* (2013.01); *H04R 1/1016* (2013.01); *H04R 1/1091* (2013.01); *H04R 25/654* (2013.01)

(58) Field of Classification Search
CPC ..... A61F 11/08; H04R 25/654; H04R 1/1016; H04R 1/1091
See application file for complete search history.

(56) References Cited

U.S. PATENT DOCUMENTS

| | | | |
|---|---|---|---|
| 3,359,535 A | 12/1967 | Webb et al. |
| 3,662,124 A | 5/1972 | Hassler et al. |
| 3,749,853 A | 7/1973 | Ely et al. |
| 3,777,079 A | 12/1973 | Fischer et al. |
| 3,868,572 A | 2/1975 | Kaufman et al. |
| 3,963,881 A | 6/1976 | Fraim et al. |
| 4,683,587 A | 7/1987 | Silverman |
| 5,222,050 A | 6/1993 | Marren et al. |
| 6,961,434 B2 | 11/2005 | Silverman |

(Continued)

FOREIGN PATENT DOCUMENTS

| | | |
|---|---|---|
| GB | 1216010 | 12/1970 |
| KR | 20090009617 | 9/2009 |
| WO | WO 2012/099756 | 7/2012 |

OTHER PUBLICATIONS

PCT Search Report, PCT/US2015/040243, dated Sep. 10, 2015, 3 pages.
Siemens—Aquaris™ Consumer Brochure, 2012.

*Primary Examiner* — Muhammad N Edun

(57) ABSTRACT

Water resistant acoustic ports and electronic hearing protection devices incorporating such ports are described. More specifically, water proof acoustic ports that provide water protection for an internal sealed chamber by providing acoustically transparent inlets that are capable of withstanding external water pressure at given depth due to their volume relation to that of the internal chamber, as well as hearing protection devices incorporating such ports, are described.

18 Claims, 2 Drawing Sheets

(56) References Cited

U.S. PATENT DOCUMENTS

| | | | |
|---|---|---|---|
| 7,267,847 B2 | 9/2007 | Karamuk | |
| 7,702,124 B2 | 4/2010 | Niederdraenk et al. | |
| 8,494,200 B2 | 7/2013 | Ram et al. | |
| 2007/0280053 A1* | 12/2007 | Polany | H04B 11/00 367/131 |
| 2010/0322452 A1 | 12/2010 | Ladabaum et al. | |
| 2015/0189963 A1* | 7/2015 | Lai | A45C 13/008 224/191 |
| 2015/0289042 A1* | 10/2015 | Yamaguchi | H04R 1/086 381/87 |

* cited by examiner

WATER RESISTANT ACOUSTIC PORT IN EAR-MOUTHED HEARING DEVICE

FIELD

The present description relates to ports used in hearing devices, and more specifically, water resistant acoustically transparent ports in ear-mounted hearing devices.

BACKGROUND

The use of hearing protective and noise attenuating devices are well known, and various types of devices have been considered. Such devices include earplugs and semi-aural devices that may be inserted into, or placed over, the ear canal of a user to obstruct passage of sound waves to the inner ear. Certain hearing devices may contain microphones for sensing sounds from the external environment and re-transmitting to the user's ear using a speaker in the protective device. A challenge with such a system is how to properly receive all sound from the external environment while protecting the microphone and its surroundings from water intrusion.

SUMMARY

In one aspect, the present description relates to a water resistant acoustic port. The water resistant acoustic port includes a housing, a sealed chamber within the housing, an inlet microtube positioned in the wall of the housing and a hydrophobic coating that covers at least a portion of the walls of the inlet microtube. The chamber has a volume, $V_C$. The inlet microtube fluidically connects the chamber to an environment external to the housing and has an inlet microtube volume, $V_I$. The inlet microtube volume is sized to be greater than or equal to the combined volume of $V_C$ and $V_I$ multiplied by the quantity (1−(External pressure in air/External pressure when submerged)). In some embodiments, the weatherproof acoustic port may further include at least a second inlet microtube positioned in the wall of the housing. The second inlet microtube may, as with the first inlet microtube, also be fluidically connect the chamber to the environment external to the housing and also be covered with a hydrophobic coating. The volume of the second inlet microtube is also a portion of the inlet microtube volume.

In another aspect, the present description relates to a weatherproof acoustic port that includes a housing, a sealed chamber within the housing, an inlet microtube positioned in the wall of the housing and a semi-permeable diverter positioned on the surface of the housing over the inlet microtube. The inlet microtube fluidically connects the chamber to an environment external to the house and has an inlet microtube volume and is capable of resisting water intrusion from ambient water at a submersion of at least one meter. The semi-permeable diverter further protects the inlet microtube from water intrusion due to an impulse event. In some embodiments, the inlet microtube is one of a plurality of inlet microtubes and the diverter is positioned over all of the inlet microtubes.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as forming a "coincident interface" with, or being "on," "connected to," "coupled with," "stacked on" or "in contact with" another element, component or layer, it can be directly on, directly connected to, directly coupled with, directly stacked on, in direct contact with, or intervening elements, components or layers may be on, connected, coupled or in contact with the particular element, component or layer, for example. When an element, component or layer for example is referred to as being "directly on," "directly connected to," "directly coupled with," or "directly in contact with" another element, there are no intervening elements, components or layers for example.

Figure 1:
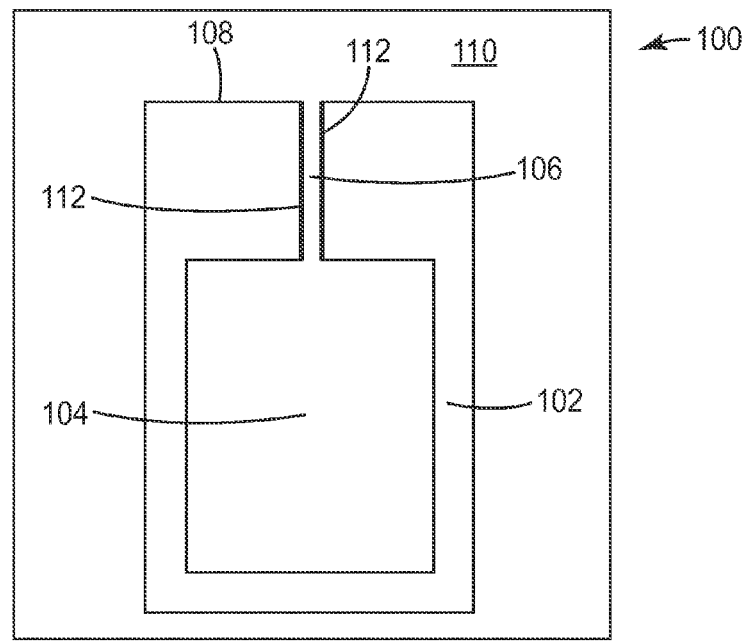
FIG. 1 is a cross-sectional view of an acoustic port according to the present description.

FIG. 1 illustrates a cross-sectional view of a water resistant acoustic port 100 according to the present description. Water resistant acoustic port 100 includes a housing 102, and a sealed chamber 104 that is located within the housing. Housing 102 may be made up of any number of appropriate materials that allow the housing to be molded into an appropriate shape and enable a potentially hollow chamber within, for example plastic materials, such as ABS or polypropylene, amongst others. The housing may be made up of thermoform or thermoset polymers. Additionally, housing 102 could be formed of composites, alloys, or other materials. In some embodiments, the housing may be constructed from multiple different materials, such that, e.g., the material surrounding the inlet microtubes is different from that in the remainder of the housing. Chamber 104 will be understood to have a given volume, $V_C$. In some embodiments, the volume of chamber may be between about 5 mm$^3$ and about 10 mm$^3$, though smaller or larger volumes may be appropriate. Water resistant acoustic port further includes an inlet microtube 106 that is positioned in the wall 108 of the housing. Inlet microtube 106 fluidically connects the chamber 104 to an environment 110 that is external to the housing. For purposes of this description, a "sealed chamber" means that the chamber is entirely sealed with the exception of the inlet microtubes that connect it to the external environment. As the acoustic port will generally be part of a wearable electronic hearing protection device, the external environment will be that in which the user is surrounded. Accordingly, at times, the external environment may be air. At other times, the external environment may be water, e.g., when the user wearing the hearing protection device happens to be submerged. Inlet microtube also has a given volume $V_I$. In one embodiment, the inlet microtube volume, $V_I$, is greater than 10% of the chamber volume, $V_C$. Generally, the inlet microtube volume will be between about 0.5 mm$^3$ and about 1.0 mm$^3$, though again, $V_I$ can be larger or smaller in certain embodiments.

Additionally, a hydrophobic coating 112 can cover at least a portion of the walls of the inlet microtube 106. This hydrophobic coating 112 may, in some embodiments, be a 3M Novec™ Coating, such as 3M Novec™ 1720 (from 3M Company, St. Paul, Minn.), though other low surface energy coatings may also be appropriate. The hydrophobic coating works to prevent capillary action in the inlet microtube from water external to or partially filling the inlet microtube. Capillary action occurs when the adhesive forces between water and a tube wall exceed the cohesive forces between the water and the molecules themselves. The greater the affinity water has for a material, the greater the distance water will travel into a tube. The height to which the water will rise and fall in a capillary tube is given by Jurin's Law. The height, h, of a liquid column is given by Equation 1:

$$h = \frac{2\gamma\cos\theta}{\rho g r} \quad \text{Equation 1}$$

where $\gamma$ is the liquid surface tension, $\theta$ is the contact angle of the liquid on the tube wall, $\rho$ is the density of the liquid, g is local acceleration due to gravity, and r is the radius of the tube.

The $\cos(\theta)$ term can take on any value between $-1$ and $+1$, and therefore dramatically impacts the extent to which water will migrate into the tube. Material with an angle of $\theta > 90$ degrees is considered hydrophobic. When the contact angle exceeds 150 degrees, the material is considered superhydrophobic. The plastic material used in some embodiments of the acoustic port housing has a contact angle with water of less than 90 degrees. This may enable capillary action which can act to either pre-fill the inlet microtube or microtubes with some water, in which case a subsequent immersion of the acoustic port into water could cause flooding of the chamber, or a "bridging over" of the inlet microtubes. It has been founded that treating the inlet microtubes with a hydrophobic coating ensures that the contact angle rises above 100 degrees, and avoids these issues with capillary action.

The combination of the inlet microtube volumes noted along with the use of a hydrophobic coating allows the acoustic port to be essentially waterproof up to certain depths. In at least some embodiments described herein, the inlet microtube or inlet microtubes in the case of a plurality of inlet microtubes (as discussed below) are capable of withstanding water intrusion into the cavity at a submersion depth of 1 m. One of skill in the art will understand that this means that the water resistant acoustic port is capable of meeting IP-67 standards. Despite its ability to prohibit water intrusion, the water resistant acoustic port of the present description is sound transparent, i.e., compression waves of air are capable of traveling substantially unrestricted through the port.

Figure 2:
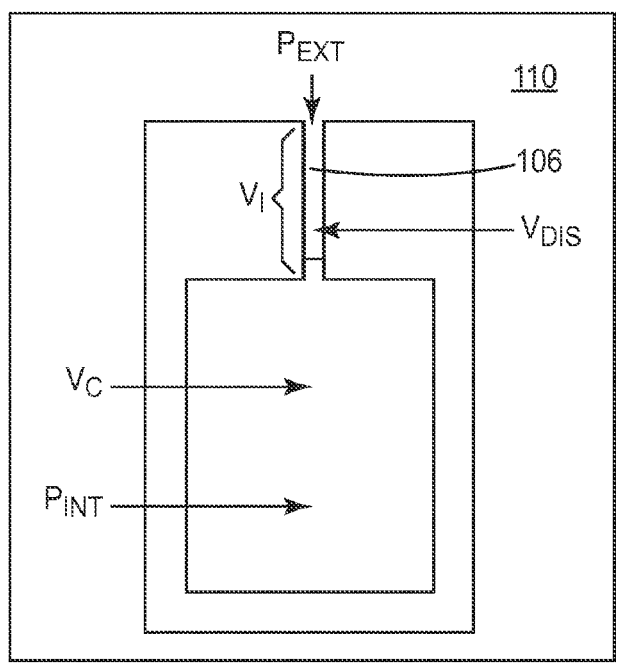
FIG. 2 is a cross-sectional view of an acoustic port according to the present description.

The ability to waterproof the acoustic port is due, in part, to the creation of a pressure differential between the chamber and external environment which aids in prohibiting water intrusion from the external environment into the chamber. FIG. 2 illustrates a cross-sectional view of a water resistant acoustic port according to the present description in an external environment 110 of water. As water moves down inlet microtube 106, it displaces air in the inlet $V_{DIS}$, which results in compression of the air in the chamber volume, $V_C$. This compression raises the air pressure $P_{INT}$ of the internal volume. The system will reach equilibrium once the external water pressure $P_{EXT}$ (determined by submersion depth) is balanced by the internal air pressure. As long as the increase in water pressure does not force water past the entirety of the inlet microtube and into the chamber, water present in the inlet microtube will be expelled when the acoustic port returns to an external environment of air. We can refer to total internal volume of the device as V, made up of volume of the inlet ($V_I$) and volume of the chamber ($V_C$) ($V = V_I + V_C$). If we define further that the external pressure above water is $P_a$ and the external pressure submerged is $P_s$, and further that the total volume V of air above water is understood as $V_a$ and submerged is $V_s$, the ideal gas law tells us the following (assuming a temperature being held constant):

$$\frac{P_s}{P_a} = \frac{V_a}{V_s} \quad \text{Equation 2}$$

In order to keep water from entering the chamber, the overall reduction in volume ($V_a - V_s$), must be less than the inlet microtube volume $V_I$. Therefore, to ensure that water does not enter the chamber:

$$V_I \geq V_a - V_s \quad \text{Equation 3:}$$

Solving Equation 1 for $V_s$ yields Equation 4:

$$V_s = \frac{P_a}{P_s} * \frac{V_a}{1} \quad \text{Equation 4}$$

Substituting the value of $V_s$ from Equation 3 into Equation 2 yields the following:

$$V_I \geq V_a * \left(1 - \frac{P_a}{P_s}\right) \quad \text{Equation 5}$$

Therefore, the aggregate volume of the inlet microtube or microtubes, $V_I$, must be greater than or equal to the volume of the inlet and chamber at above water conditions multiplied by the quantity of (1−the external pressure in air over the external pressure when submerged). Satisfying this condition will result in water not traversing the entirety of the inlet microtube(s), and thus not entering the sealed chamber. In other words, the acoustic port is essentially "waterproof." The volume of the inlet microtube or microtubes in the present invention is chosen according to the relationship in Equation 5.

Figure 3:
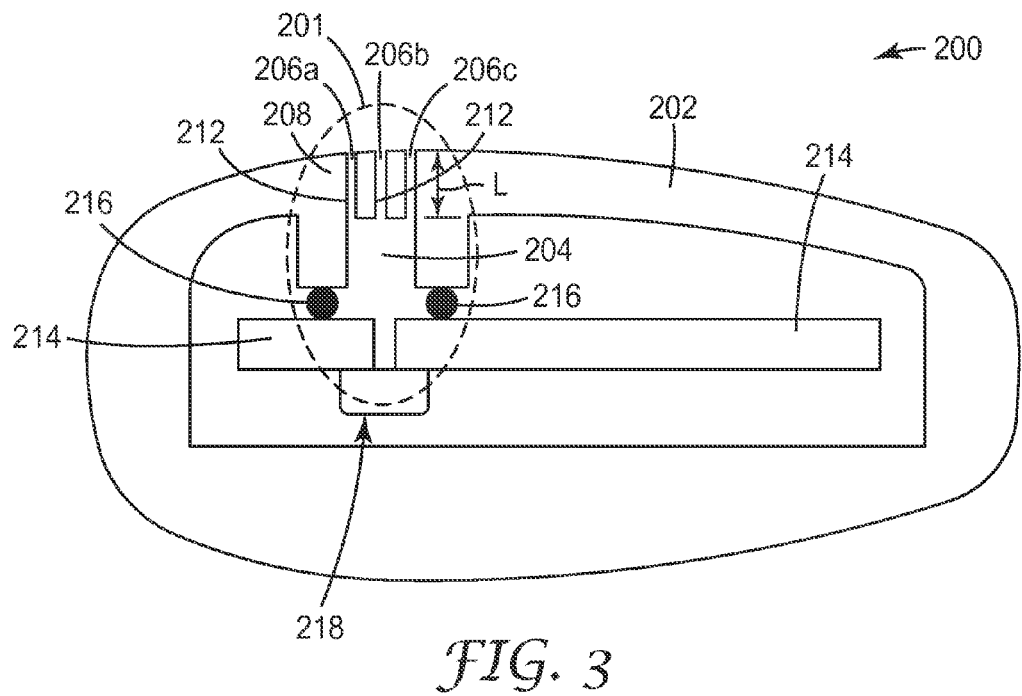
FIG. 3 is a cross-sectional view of an electronic hearing protection device according to the present description.

A different embodiment of an acoustic port as well as device in which it may be implemented, is provided in FIG. 3. Electronic hearing protection device 200 includes acoustic port 201. In this embodiment, weatherproof acoustic port includes a first inlet tube 206a as well as a second inlet microtube 206b, each of which is positioned in the wall 208 of housing 202. In some embodiments, as illustrated, the acoustic port may include a third inlet microtube 206c, or any other appropriate number of inlet microtubes, such as 4, 5, 6, 7, 8, 9, 10 or potentially more. The second inlet microtube fluidically connects the sealed chamber 204 to the environment that is external to the housing. As with the embodiment in FIG. 1, the second inlet microtube, like the first inlet microtube is covered with a hydrophobic coating 212. In this embodiment, where more than one inlet microtube is present, the total volume of each microtube is added to provide the total $V_I$. In other words, the inlet microtube volume, $V_I$ is the sum of the volumes of inlets 206a, 206b and 206c. The length, L of the inlet microtubes will generally be substantially similar. In one embodiment, the first inlet and second inlet microtubes (as well as the third inlet microtube) will have a length of between about 0.9 and 1.25 mm. It is desirable that the inlet microtube or microtubes not be excessively long. This may result in resonance in the tubes, as well as excessive acoustic impedance. Both of the issues will impact the fidelity of the sound field in the chamber, which, as discussed in FIG. 3, may be captured by a microphone.

FIG. 3 provides further potential detail of acoustic port 201. Sealed chamber 204 is surrounded in part by housing 202 and inlet microtubes 206a, 206b and 206c. However, the chamber may further be surrounded by additional elements, for example, a printed circuit board 214 as illustrated in FIG. 3. Additionally, the chamber 204 may be in part surrounded by a seal 216 that separates the housing 202 and circuit board 214. Circuit board 214 may be an electronic printed circuit board assembly (PCBA). In one embodiment, the seal 216 may be an O-ring. Other appropriate seals, such as other gasket materials, may also be utilized. Additionally, the chamber may, in part, be surrounded by a microphone 218 that is positioned beneath, and connected to, circuit board 214. The microphone may in one embodiment, be a MEMS type microphone and may be connected to the circuit board by soldering the bottom side of it to the microphone. This microphone may be used to gather the sound that enters acoustic port 201. The sound may then be re-transmitted by a speaker out a separate sound-emitting opening (not shown) that is positioned within the ear canal of a user.

Figure 4:
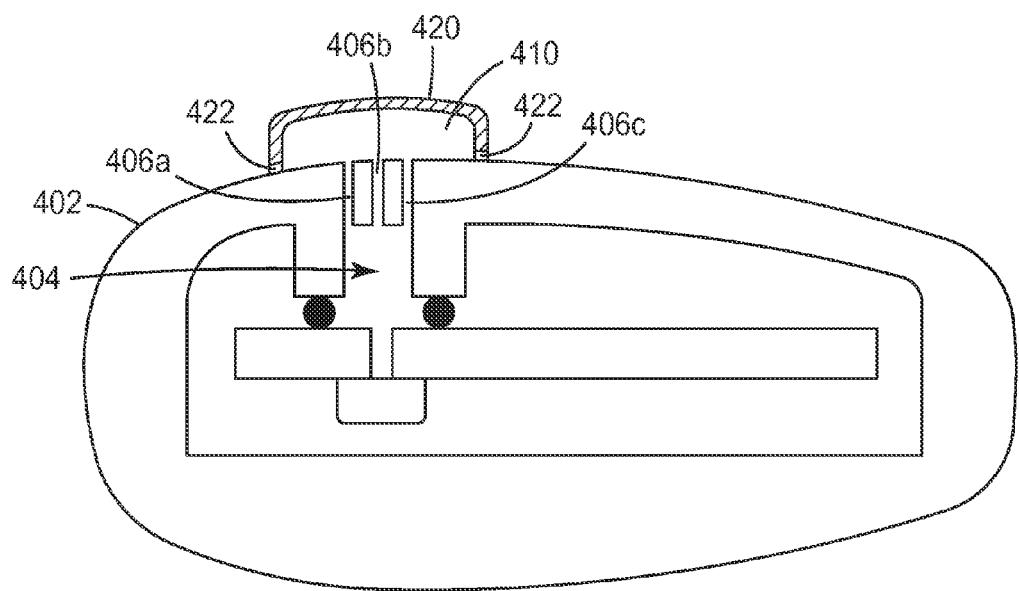
FIG. 4 is a cross-sectional view of an electronic hearing protection device according to the present description.

FIG. 4 offers further illustration of certain embodiments of the invention. Here, acoustic port again includes a first inlet microtube 406a, and may further include a second inlet microtube 406b and potentially third inlet microtube 406c, as well as potential further inlet microtubes. In this embodiment, the inlet microtube may not have a hydrophobic coating on the walls of the inlet microtubes. As before, inlet microtube or tubes separate the chamber 404 from the external environment 410. However, in this embodiment, the water resistant acoustic further includes a semi-permeable diverter 420 that is positioned on the surface of the housing 402 over the inlet microtube 406a, or tubes 406a, 406b, 406c such that the semi-permeable diverter 420 eliminate line of sight path to the inlet microtube. The diverter includes small openings 422 that are positioned on sides of the diverter. As such water simply impacting the top of the port will be unable to travel unimpeded into the acoustic port with force. The diverter will likely only be subject to permeation when the acoustic port is submerged. This semi-permeable diverter offers the further protection of protecting the sealed chamber from water intrusion due, not to submersion, but to an impulse event, such as contact with water at a high velocity. Such an impulse event may create peak forces greater than that of water, e.g., at a depth of 1 m, and may flood the inlet microtubes reaching the chamber absent the diverter's presence.

We claim:

1. A water resistant acoustic port, comprising:
a housing
a sealed chamber within the housing, the chamber having a volume ($V_C$), and
an inlet microtube positioned in the wall of the housing and fluidically connecting the chamber to an environment external to the housing, the inlet microtube having an inlet microtube volume ($V_I$);
a hydrophobic coating that overlaps at least a portion of walls of the inlet microtube;
wherein the inlet microtube volume is greater than or equal to the combined volume of $V_C$ and $V_I$ multiplied by the quantity (1−(External pressure in air/External pressure when submerged)).

2. The water resistant acoustic port of claim 1, further comprising at least a second inlet microtube positioned in the all of the housing, the second inlet microtube also connecting the chamber to the environment external to the housing and also being covered with a hydrophobic coating, wherein the volume of the second inlet tube is also a portion of the inlet microtube volume, $V_I$.

3. The water resistant acoustic port of claim 2, wherein the inlet and second inlet have a length of between about 0.9 and about 1.25 mm.

4. The water resistant acoustic port of claim 1, wherein $V_I$ is between about 0.5 mm$^3$ and about 1.0 mm$^3$.

5. The water resistant acoustic port of claim 1, wherein $V_C$ is between about 5 mm$^3$ and about 10 mm$^3$.

6. The water resistant acoustic port of claim 1, further comprising a semi-permeable diverter positioned on the surface of the housing over the inlet microtube eliminating line of sight path to the inlet microtube.

7. The water resistant acoustic port of claim 6, wherein the semi-permeable diverter comprises small openings on sides of the diverter.

8. The water resistant acoustic port of claim 6, wherein the semi-permeable diverter protects the inlet microtubes from water intrusion due to an impulse event.

9. The water resistant acoustic port of claim 1, wherein the water resistant acoustic port is sound transparent.

10. The water resistant acoustic port of claim 1, wherein the inlet microtube is capable of withstanding water intrusion into the cavity at a submersion depth of up to 1 m.

11. The water resistant acoustic port of claim 1, wherein the hydrophobic coating prevents capillary action in the inlet microtube.

12. The water resistant acoustic port of claim 1, wherein a pressure differential between the chamber and external environment aids in prohibiting water extrusion from the external environment into the chamber.

13. The water resistant acoustic port of claim 1, wherein the chamber is surrounded by the housing, inlet microtubes, a printed circuit board, a seal separating the housing and circuit board, and a microphone positioned beneath the circuit board.

14. An electronic hearing protection device comprising the water resistant acoustic port of claim 13, and an earpiece that includes a sound-emitting opening that may be positioned within the ear canal of a user.

15. The water resistant acoustic port of claim 1, wherein $V_I$ is at least 10% of $V_C$.

16. A water resistant acoustic port, comprising:
a housing;
a sealed chamber within the housing;
an inlet microtube positioned in the wall of the housing and connecting the chamber to an environment external to the housing, the inlet microtube being generally capable of resisting water intrusion from ambient water at a submersion of at least one meter, wherein the inlet microtube further comprises a hydrophobic coating that overlaps at least a portion of the internal surfaces of the inlet microtube to reduce capillary effects; and
a semi-permeable diverter positioned on the surface of the housing over the inlet microtube, herein the semi-permeable diverter further protects the inlet microtube from water intrusion due to an impulse event.

17. The water resistant acoustic port of claim 16, wherein the inlet microtube is one a plurality of inlet microtubes and the diverter is positioned over all of the inlet microtubes.

18. The water resistant acoustic port of claim 17, wherein the total volume of the plurality of inlet microtubes, $V_I$ is at least 10% of the volume of the chamber within the housing, $V_C$.

* * * * *

UNITED STATES PATENT AND TRADEMARK OFFICE
CERTIFICATE OF CORRECTION

PATENT NO. : 9,636,259 B2  
APPLICATION NO. : 14/798516  
DATED : May 2, 2017  
INVENTOR(S) : Paul Henry Page 1 of 1

It is certified that error appears in the above-identified patent and that said Letters Patent is hereby corrected as shown below:

On the Title Page

Column 1 (Title)
Line 2 (approx.), delete "EAR-MOUTHED" and insert -- EAR-MOUNTED --, therefor.

In the Specification

Column 1
Line 2, delete "EAR-MOUTHED" and insert -- EAR-MOUNTED --, therefor.

Signed and Sealed this
Twenty-fourth Day of April, 2018

Andrei Iancu
*Director of the United States Patent and Trademark Office*